(12) United States Patent
Kim et al.

(10) Patent No.: US 8,697,366 B2
(45) Date of Patent: Apr. 15, 2014

(54) ANTI-CANCER DRUG SCREENING METHOD USING RORα

(75) Inventors: Keun Il Kim, Seoul (KR); Ji Min Lee, Seoul (KR); Sung Hee Baek, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 0 days.

(21) Appl. No.: 13/143,676

(22) PCT Filed: Jan. 8, 2010

(86) PCT No.: PCT/KR2010/000132
§ 371 (c)(1),
(2), (4) Date: Aug. 23, 2011

(87) PCT Pub. No.: WO2010/079994
PCT Pub. Date: Jul. 15, 2010

(65) Prior Publication Data
US 2011/0294130 A1    Dec. 1, 2011

(30) Foreign Application Priority Data
Jan. 8, 2009 (KR) ........................ 10-2009-0001519

(51) Int. Cl.
*G01N 33/53* (2006.01)
*G01N 33/574* (2006.01)

(52) U.S. Cl.
USPC .......................................... 435/7.1; 435/7.23

(58) Field of Classification Search
None
See application file for complete search history.

(56) References Cited

U.S. PATENT DOCUMENTS

2004/0023267 A1*   2/2004   Morris .............................. 435/6
2005/0165218 A1*   7/2005   Beerli et al. .................. 530/350

FOREIGN PATENT DOCUMENTS

WO    WO 2008021549 A2 *   2/2008

OTHER PUBLICATIONS

Duplus et al., J. Neurochemistry., 2008, 104:1321-1332.*
Chauvet et al., "Retinoic acid receptor-related orphan receptor (ROR) alpha4 is the predominant isoform of the nuclear receptor RORalpha in the liver and is up-regulated by hypoxia in HepG2 human hepatoma cells," Biochem J. 364(2):449-456 (2002).
Chauvet et al., "The gene encoding human retinoic acid-receptor-related orphan receptor alpha is a target for hypoxia-inducible factor 1," Biochem J. 384(1):79-85 (2004).
Karasek et al., "Expression of melatonin MT (1) and MT (2) receptors, and ROR alpha (1) receptor in transplantable murine Colon 38 cancer," Neuro Endocrinol Lett. 23(Suppl 1):55-60 (2002). Abstract only provided.
Matysiak-Scholze et al., "The structural integrity of ROR alpha isoforms is mutated in staggerer mice : Cerebellar coexpression of ROR alpha1 and ROR alpha4," Genomics. 43(1):78-84 (1997). Abstract only provided.
Moretti et al., "Role of the orphan nuclear receptor ROR alpha in the control of the metastatic behavior of androgen-independent prostate cancer cells," Oncol Rep. 9(5):1139-1143 (2002). Abstract only provided.
Winczyk et al., "Possible involvement of the nuclear RZR/ROR-alpha receptor in the antitumor action of melatonin on murin Colon 38 cancer," Tumour Biol. 23(5):298-302 (2002). Abstract only provided.
International Search Report for International Patent Application No. PCT/2010/000132, dated Sep. 28, 2010 (4 pages).

* cited by examiner

*Primary Examiner* — Hong Sang
(74) *Attorney, Agent, or Firm* — Clark & Elbing LLP

(57) ABSTRACT

The present invention relates to a method for screening an anticancer agent using RORα, the method comprising the steps of: culturing cells; bringing a potential substance into contact with the cells; determining whether the phosphorylation level of RORα in the cells increases as compared to that in control cells (not brought into contact with the potential substance); and selecting the potential substance as an anticancer agent if the phosphorylation level of RORα in the cells increases.

3 Claims, 9 Drawing Sheets

Figures 1A-1F

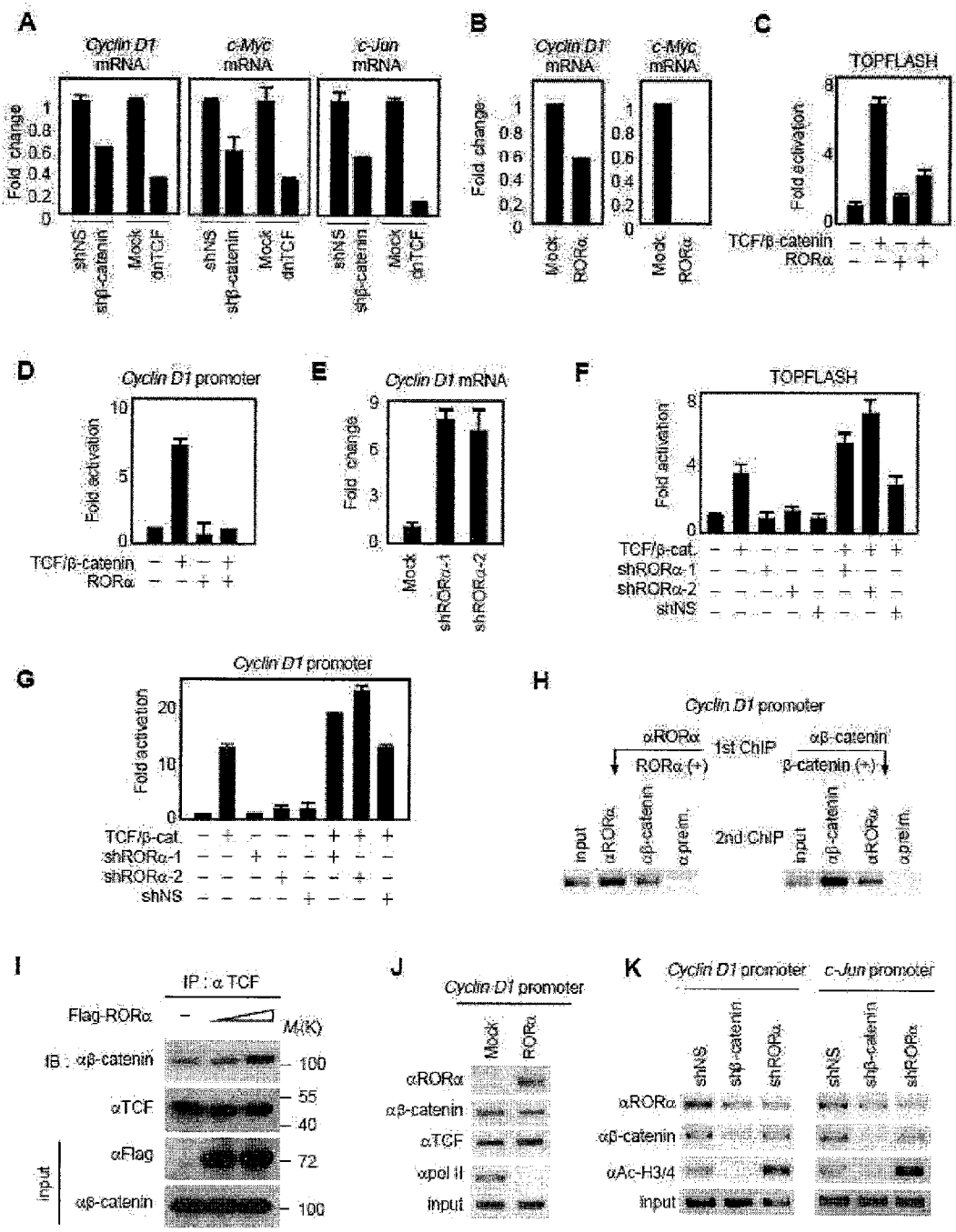

Fig. 6
A
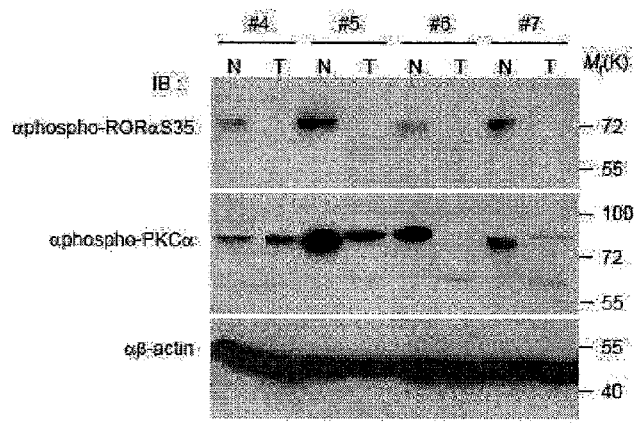
B
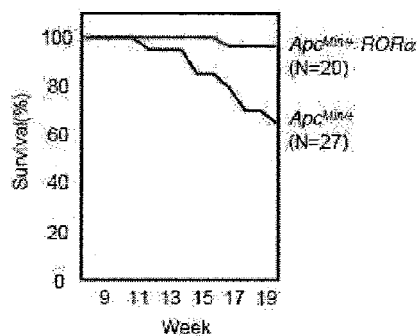
C
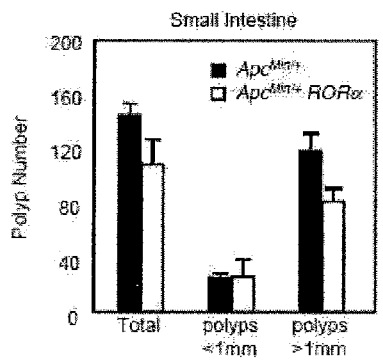
D
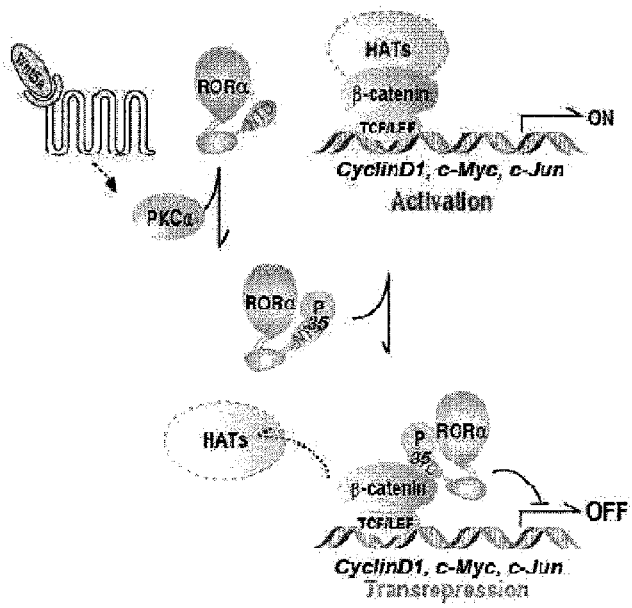

ANTI-CANCER DRUG SCREENING METHOD USING RORα

BACKGROUND OF THE INVENTION

1. Technical Field

The Wnt genes encode a large family of cysteine-rich secreted polypeptides that mediate diverse signalling processes. Aberrant activation of Wnt signaling plays important roles as a major driving force linked to developmental defects and tumorigenesis (Klaus and Birchmeier, 2008; Korinek et al., 1997; Morin et al., 1997; Willert et al., 2003). Wnt signaling pathways have been divided into two categories; one is the canonical Wnt/β-catenin signaling pathway and the other is the noncanonical Wnt/$Ca^{2+}$ signaling pathway (Kühl et al., 2000; Liang et al., 2007; Liu et al., 2005). In the absence of Wnt activation, the level of β-catenin in the cytoplasm remains low due to the degradation of β-catenin by 26S proteasome after paired phosphorylation through casein kinase I (CKI) and glycogen synthase kinase-3β (GSK-3β) (Orford et al., 1997; Salic et al., 2000). The canonical Wnts bind to the Frizzled (Frz) family proteins and low-density lipoprotein receptor-related (LRP) 5 or 6, and this binding activates disheveled (Dvl) and inhibits the activity of GSK-3β; this inhibition results in the stabilization and subsequent translocation of β-catenin to the nucleus for the regulation of target gene expression with T-cell factor (TCF)/lymphoid enhancer factor (LEF) (Behrens et al., 1996; Giles et al., 2003; Molenaar et al., 1996; Moon et al., 2002).

Noncanonical Wnt signaling pathways affected by Wnt ligands such as Wnt5a have diverse and occasionally opposing roles (Slusarski et al., 1997; Tones et al., 1996). Noncanonical Wnts are both antagonistic and synergistic to canonical Wnt signalling pathway depending on their receptor context. Wnt5a-deficient mice show increased β-catenin signaling in the distal limb, indicating that Wnt5a is involved in the negative regulation of the Wnt/β-catenin signaling pathway (Nemeth et al., 2007). In contrast, Wnt5a has been shown to activate Wnt/β-catenin signaling in the presence of Frz4 and LRP5 (Mikels and Nusse, 2006). Given that the activation of the noncanonical Wnt signaling pathway results in intracellular $Ca^{2+}$ release and activation of $Ca^{2+}$ sensitive enzymes such as $Ca^{2+}$/calmodulin-dependent kinase II (CaMKII) and protein kinase C (PKC), the noncanonical Wnt pathways are apparently different from the canonical Wnt pathway.

2. Background Art

A mouse model of spontaneous intestinal tumorigenesis, designated $APC^{min/+}$, is widely used to explore Wnt/β-catenin signalling (Fodde et al., 1994; Shibata et al., 1997; Su et al., 1992). The genetic basis of familial associated polyposis (FAP) was mapped to the adenomatous polyposis coli (APC) gene, and germline and sporadic mutations in APC occur in most of FAP (Groden et al., 1991; Kinzler et al., 1991). $APC^{min/+}$ mice have a mutation in the APC gene causing hyperactivation of Wnt/β-catenin signaling and die within 6 months from severe intestinal tumor development. As Wnt/β-catenin signaling is crucial for the maintenance of cellular homeostasis, a variety of positive and negative cellular regulators have been identified using genetic, proteomic, and RNA interference-based screening approaches. Runx3 forms a ternary complex with TCF4/β-catenin and suppresses the DNA binding activity of TCF4/β-catenin (Ito et al., 2008). Wilms tumor suppressor WTX antagonizes Wnt/β-catenin signalling by promoting ubiquitination and degradation of β-catenin (Major et al., 2007). Recently, CDK8, a cyclin-dependent kinase member of the mediator complex, has been shown to be necessary for β-catenin-driven transcriptional activation (Firestein et al., 2008). Given that dysregulated transcriptional activity of β-catenin is crucial for colorectal tumorigenesis and progression, identification of genes that are responsible for genetic perturbations is important to explore complex malignant processes.

Members of the orphan nuclear receptor family play various roles in signal integration, including modulation of neurogenesis, homeostasis, and disease by regulating subsets of gene expression both positively and negatively (Blumberg and Evans, 1998; Giguère, 1999; Mangelsdorf et al., 1995). The retinoic acid-related orphan nuclear receptor (ROR)α is a member of the orphan nuclear receptor family for which no cognate ligands have been identified thus far (Giguère et al., 1994; Gold et al., 2003; Lau et al., 1994). Staggerer (sg) is a classical mutation of the RORα gene that blocks Purkinje cell differentiation, resulting in cerebellar hypoplasia and congenital ataxia (Hamilton et al., 1996). Sg mice exhibits phenotypes regarding lipid metabolism, bone metabolism, hyperinflammatory responses, and mainly cerebellar development and approximately 50% of the mice die shortly after weaning, which makes studying RORα function with Sg mice very difficult (Doulazmi et al., 2006).

Given that nuclear receptors function as potent regulators of normal physiology as well as pathologies such as cancer, the orphan nuclear receptors can functionally interact with potent oncogenic systems, for example, the Wnt and PKC signaling pathways (Peifer and Polakis, 2000). This interaction might elicit changes in oncogenesis and cellular adhesion (Polakis, 2000; van de Wetering et al., 2002). Compared to other classes of nuclear receptors, the function and related signaling pathways for the orphan nuclear receptor RORα have not yet been studied extensively.

Thus, the present inventors identified a critical role of RORα at the crossroads between the canonical and the non-canonical Wnt signalling pathways in attenuating β-catenin transcriptional activity in a phosphorylation-dependent manner in colon cancer, based on cell culture, colorectal carcinoma tissues, and mouse cancel model studies. Biochemical purification of RORα containing complex identifies β-catenin as a component, providing a novel link between RORα and Wnt signaling pathway. Analysis of RORα interactions with β-catenin reveals that the RORα-mediated inhibition of Wnt/β-catenin signalling requires Wnt5a/PKCα induced phosphorylation on serine residue 35 of RORα, and the binding of RORα to β-catenin is triggered and enhanced by phosphorylation of RORα. Intriguingly, reduction of phosphorylation of RORα concomitant with downregulation of PKC is correlated with activation of Wnt target genes and tumor progression in colorectal carcinoma tissues. The present inventors invented the present invention by revealing of role of RORα in transrepression of the Wnt/β-catenin signalling pathway, thereby regulating cell proliferation and tumor progression in a pathophysiological model.

SUMMARY OF THE INVENTION

It is an object of the present invention to provide a method for effectively screening an anticancer agent.

Another object of the present invention is to provide a useful method for diagnosing cancer.

The present invention provides a method for effectively screening an anticancer agent using RORα.

The present invention provides a useful method for diagnosing cancer using RORα.

The inventive method for screening a substance inducing the phosphorylation of serine in the N-terminal region of RORα is useful for identifying a cancer therapeutic agent.

Particularly, the method of the present invention may be applied to any cancer caused by the Wnt/β-catenin signal, in which the cancer is preferably colorectal cancer.

The present invention can be advantageously used to diagnose cancer by measuring the amount of RORα in vivo.

BRIEF DESCRIPTION OF THE DRAWINGS

FIG. 1. Purification of RORα-containing complex and identification of β-catenin as a binding partner (A) RORα-containing complex was purified from extracts obtained from HEK293 cells stably expressing Flag-tagged RORα. As a negative control, a mock purification from HEK293 cells stably expressing an empty vector was performed. The bound proteins were resolved by SDS-PAGE and prepared for LC-MS/MS analysis. (B) Peptide sequences of RORα-associated polypeptides obtained from LC-MS/MS analysis revealed that GRIP1 and β-catenin are components of the RORα-containing complex (SEQ ID NOs:6-15). (C) β-catenin and GRIP1 were detected from the elutes by immunoblot analysis. (D) Coimmunoprecipitation of endogenous RORα with β-catenin in HEK293 cells. (E) Ni+-NTA-agarose pulldown assay was performed with plasmids expressing each GFP-tagged β-catenin deletion construct and HisMax-RORα. (F) Illustration of the structure of various β-catenin deletion constructs and binding to RORα.

FIG. 2. Requirement of RORα in mediating transcriptional repression of β-catenin transcriptional activity (A) Real-time quantitative RT-PCR analysis of the cyclin D1, c-myc and c-jun transcripts in HCT116 cells in the presence of either shRNA against β-catenin or dominant negative TCF. (B) Measurement of cyclin D1 and c-myc transcripts after transfection of RORα in HCT116 colon cancer cells. (C and D) Overexpression of RORα inhibited the TCF/β-catenin-mediated activation of the TOPFLASH reporter (C) and cyclin D1 promoter reporter (D). (E) Measurement of mRNA abundance of cyclin D1 after knockdown of RORα by two independent shRNAs in HCT116 colon cancer cells. (F and G) Introduction of shRNAs against RORα increased the transcriptional activation of the TOPFLASH reporter (F) or the cyclin D1 promoter reporter (G). Data are represented as mean±s.d. for three independent experiments. (H) Two-step ChIP assay to determine whether RORα and β-catenin are assembled on the same promoter. (I) HCT116 cells with or without exogenous expression of RORα were coimmunoprecipitated with anti-TCF antibody and the immunoprecipitated materials were subject to immunoblotting against anti-β-catenin antibody. Interaction between TCF and β-catenin was not changed with RORα overexpression. (J) ChIP assay on the cyclin D1 promoter in HCT116 cells with or without overexpression of RORα. Occupancy of the cyclin D1 promoter by RORα, β-catenin, TCF and RNA polymerase II is indicated. (K) The shRNA-coupled ChIP assay was performed on cyclin D1 and c-jun promoters in HCT116 cells. Knockdown of β-catenin resulted in decreased histone acetylation as well as decreased recruitment of RORα on the promoters, indicating that RORα binds through β-catenin.

(A) Schematic representation of RORα showing the location of the N-terminal domain (NTD), the DNA-binding domain (DBD), the hinge region, the ligand-binding domain (LBD), and the AF-2 domain. (B) Ni+-NTA-agarose pulldown assay revealed that RORα segments that span amino acids 1-65 corresponding to NTD are sufficient to bind β-catenin. HEK293 cells were cotransfected with plasmids expressing each His-tagged RORα deletion construct and β-catenin. Whole cell extracts (left panel) and Ni+-NTA-agarose pulldown materials (right panel) were analyzed by immunoblotting against anti-β-catenin IgG or anti-Xpress IgG. (C) Illustration of the structure of deletion fragments of RORα(SEQ ID NO:17). (D) Interaction of each RORα deletion construct with HisMax-β-catenin was assessed by Ni+-NTA-agarose pulldown assay. (E) Coimmunoprecipitation of RORα with various PKC isoforms. (F) Synthesized peptides of RORα(NQESARKSE; SEQ ID NO:17) were used as substrates in the kinase assay with PKCa enzyme. The phosphorylated peptide samples were analyzed by LC-MS analysis. (G) HCT116 cells were treated with TPA at an indicated time period, and cell lysates were immunoprecipitated with anti-RORa antibody, followed by immunoblotting analysis against anti-phospho-Ser antibody indicating phosphorylated RORα☐ at endogenous level. (H) HCT116 cells were treated with TPA one day after transfection with Flag-RORα WT, S35A, or S39A. Immunoprecipitation assay was conducted with anti-Flag antibody, and the phosphorylated RORα was detected by immunoblot analysis with anti-phospho-Ser antibody. (I) In vitro kinase assays using either constitutive active form (caPCKα) or kinase deficient form of PKCα(kdPCKα) immunoprecipitated from cell lysates as the kinase and purified GST-RORα N-terminal wild-type (WT) or S35A proteins as substrates were performed. The reaction samples were subjected to 12% SDSPAGE, and phosphorylated RORα was detected by autoradiography. (J) HCT116 cells were transfected with Flag-RORα WT or S35A and stained with antibodies directed against Flag epitope. The fluorescence-conjugated secondary antibody was visualized using fluorescence microscopy, and nuclear staining with DAPI was shown.

Figure 4:
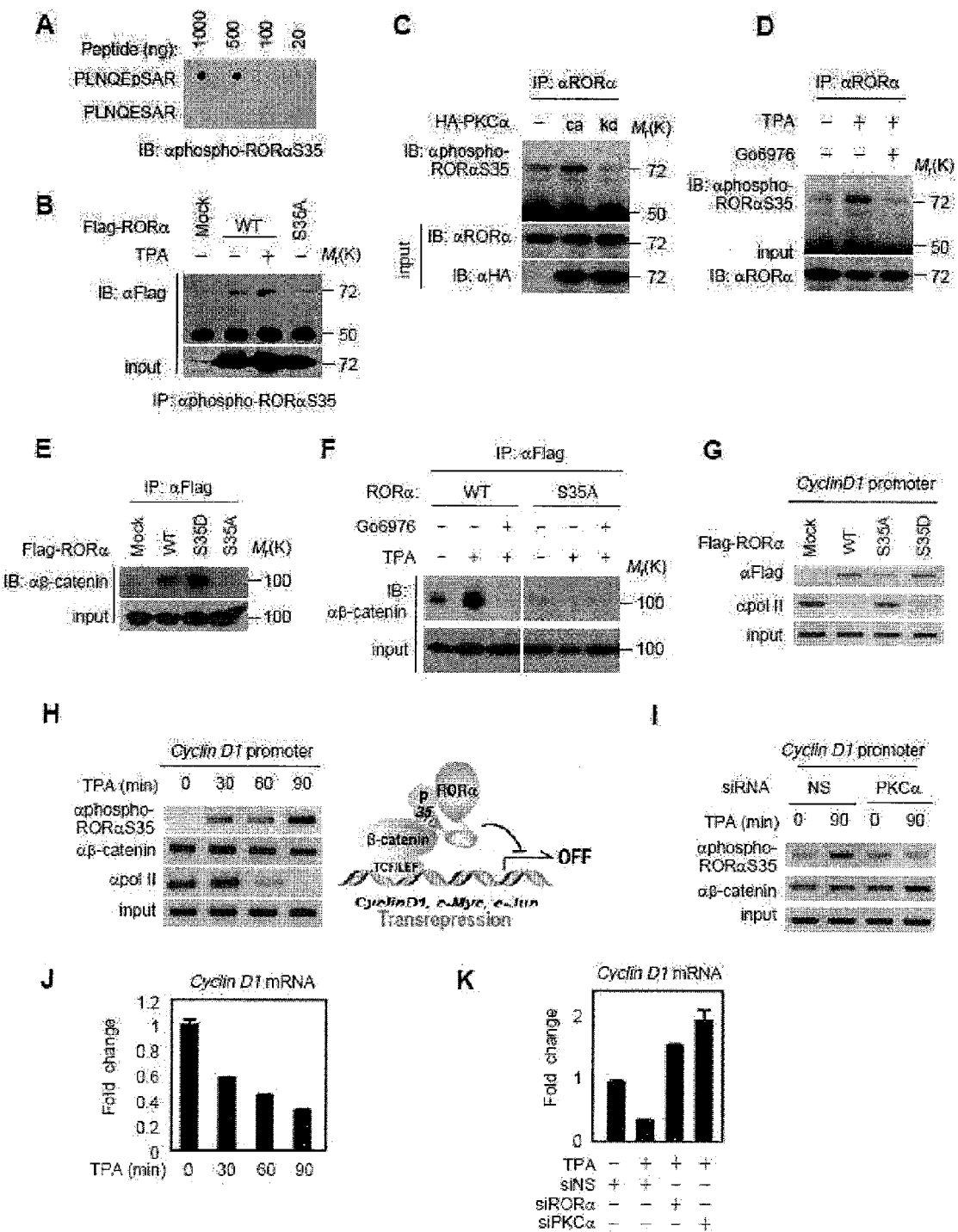

FIG. 4. PKCα-dependent phosphorylation of RORα is crucial for downregulation of Wnt/β-catenin target genes (A) The specificity of the antibody raised against phosphorylated RORαS35 peptide (SEQ ID NO:18) was assessed by dot blot analysis. (B) Treatment of TPA increased phophorylated RORα on S35 site as assessed by immunoprecipitation with anti-phospho-RORαS35 antibody. (C) Immunoblot against anti-phospho-RORαS35 antibody indicated that caPKCα increased phosphorylation of RORα, whereas kdPKCαfailed to phosphorylate RORα. (D) Treatment of Go6976, a PKCα inhibitor, abolished TPA-dependent phosphorylation of RORα as assessed by immonoblotting with anti-phospho-RORαS35 antibody. (E) HCT116 cells were transfected with Flag-RORα WT, S35D, or S35A, and the cell extracts were immunoprecipitated with anti-Flag antibody followed by immunoblotting against anti-β-catenin antibody. (F) Coimmunoprecipitation assay of β-catenin with either RORαWT or S35A in HCT116 cells after treatment with TPA in the absence or presence of Go6976. (G) ChIP analysis on the cyclin D1 promoter after transfection with Flag-RORαWT, S35A, or S35D in HCT116 cells. (H) ChIP analysis on the cyclin D1 promoter in HCT116 cells after TPA treatment for indicated time. (I) ChIP assay was performed on the cyclin D1 promoter in the absence or presence of siRNA against PKCα with treatment of TPA for 90 min. (J) Real-time quantitative RT-PCR analysis of the cyclin D1 transcript in HCT116 cells in the presence of TPA for indicated time. (K) Knockdown effect of siRNA against RORα or PKCα was assessed in the expression of the cyclin D1 transcript in HCT116 cells.

Figure 5:
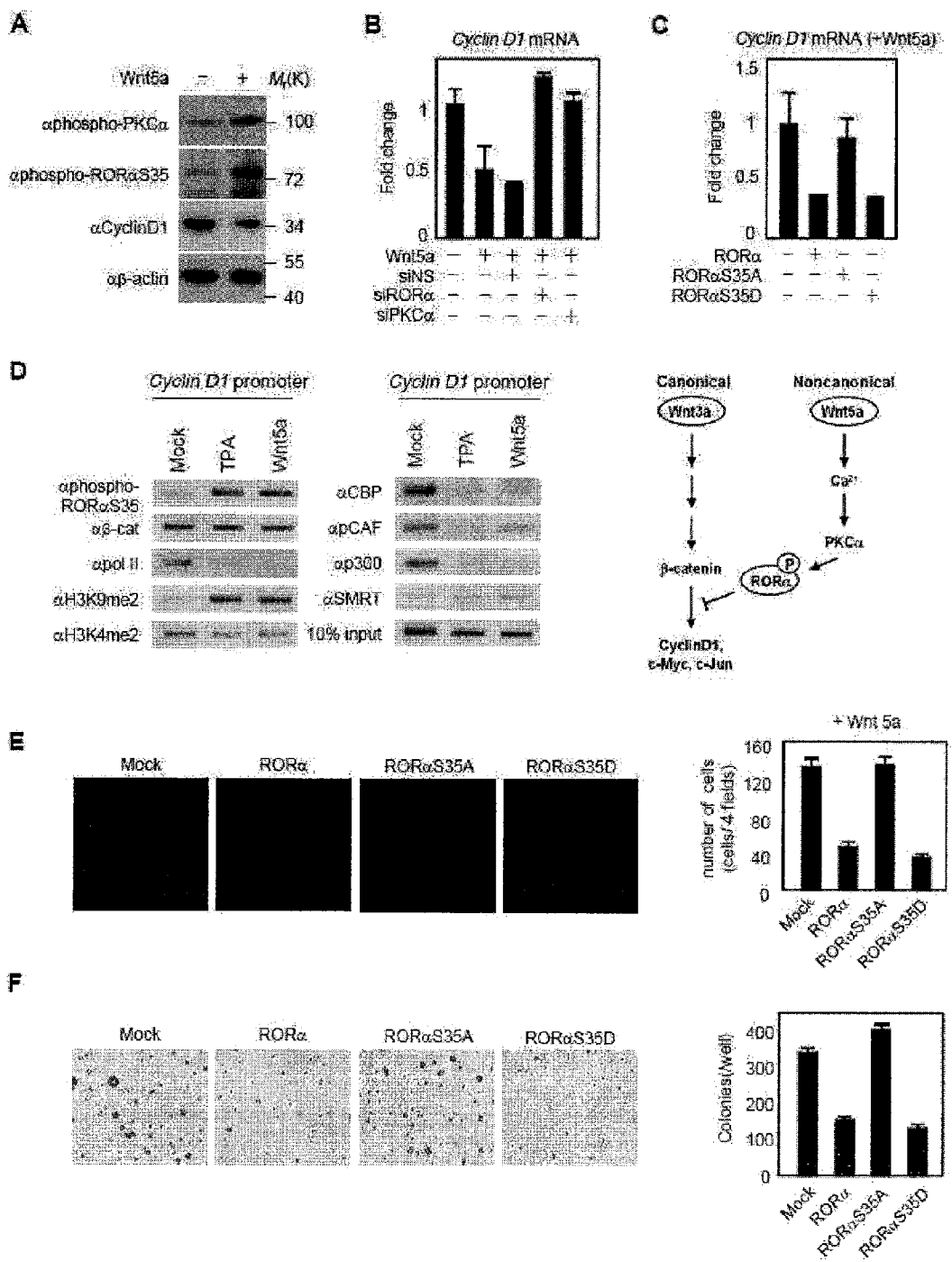

FIG. 5. Wnt5a antagonizes the canonical Wnt signaling by transrepression function of RORα

(A) Treatment of Wnt5a increased phosphorylated RORα and PKCα but decreased cyclin D1 expression as assessed by immunoblot analysis against each antibody.

(B) Cyclin D1 transcript was measured after introducing siRNAs against RORα or PKCα in the presence of Wnt5a in HCT116 cells. (C) Real-time quantitative RTPCR analysis of the cyclin D1 transcript in HCT116 cells after introducing RORα, S35A, or S35D in the presence of Wnt5a. (D) CUP assay on the cyclin D1 promoter with treatment of either TPA or Wnt5a in HCT116 cells. Occupancy of the cyclin D1 promoter by phosphorylated RORα, β-catenin, RNA polymerase II, H3K9me2, H3K4me2, CBP, pCAF, p300, or SMRT was indicated. (E) Transwell cell migration assay for RORα, RORαS35A, or RORαS35D-expressing HCT116 cells with treatment of Wnt5a. Values are represented as mean±s.d. for three independent experiments. (F) The anchorage-independent growth of HCT116 cells expressing RORα, RORαS35A, or RORαS35D in soft agar. Values are expressed as mean±SEM for two experiments in 6 place wells. Colonies were counted in 10 different fields and total colony number/well was calculated. Representative image is shown for each group.

FIG. 6. Reduction of RORα phosphorylation in human colorectal tissues and characterization of tumors in APC$^{min/+}$ mice with or without RORα

(A) Immunoblot analysis against anti-phospho-RORαS35, and anti-phospho-PKCα antibodies in human colorectal tumor tissue samples (T) along with matched normal tissue samples (N). (B) Effects of RORα on mortality in APC$^{min/+}$ mice. (C) The number of visible polyps (>1.0 mm) in the small intestine was counted by stereoscopic microscopy in age (20 to 24 weeks old)- and sex-matched APC$^{min/+}$ mice and APC$^{min/+}$ RORα transgenic mice. (D) Schematic model of downregulation of canonical Wnt signalling by Wnt5a/PKCα-dependent phosphorylation of RORα in colon cancer. RORα confers a transrepression function to the β-catenin-mediated transcriptional activation of Wnt/β-catenin target genes, such as cyclin D1, c-myc, and c-jun, by the enhanced binding to β-catenin via the phosphorylation on serine 35 residue of RORα and possibly by competing with other coactivators for binding to β-catenin. This crosstalk modulates the invasive activity of tumor cells by inhibiting Wnt target genes that are involved in tumor progression, proliferation, and growth.

Figure 7:
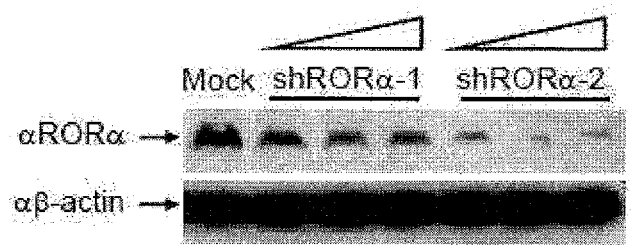

FIG. 7 shows validation of shRNAs against RORα Knockdown of RORα by two different types of shRNAs was validated by immunoblotting analysis.

Figure 8:
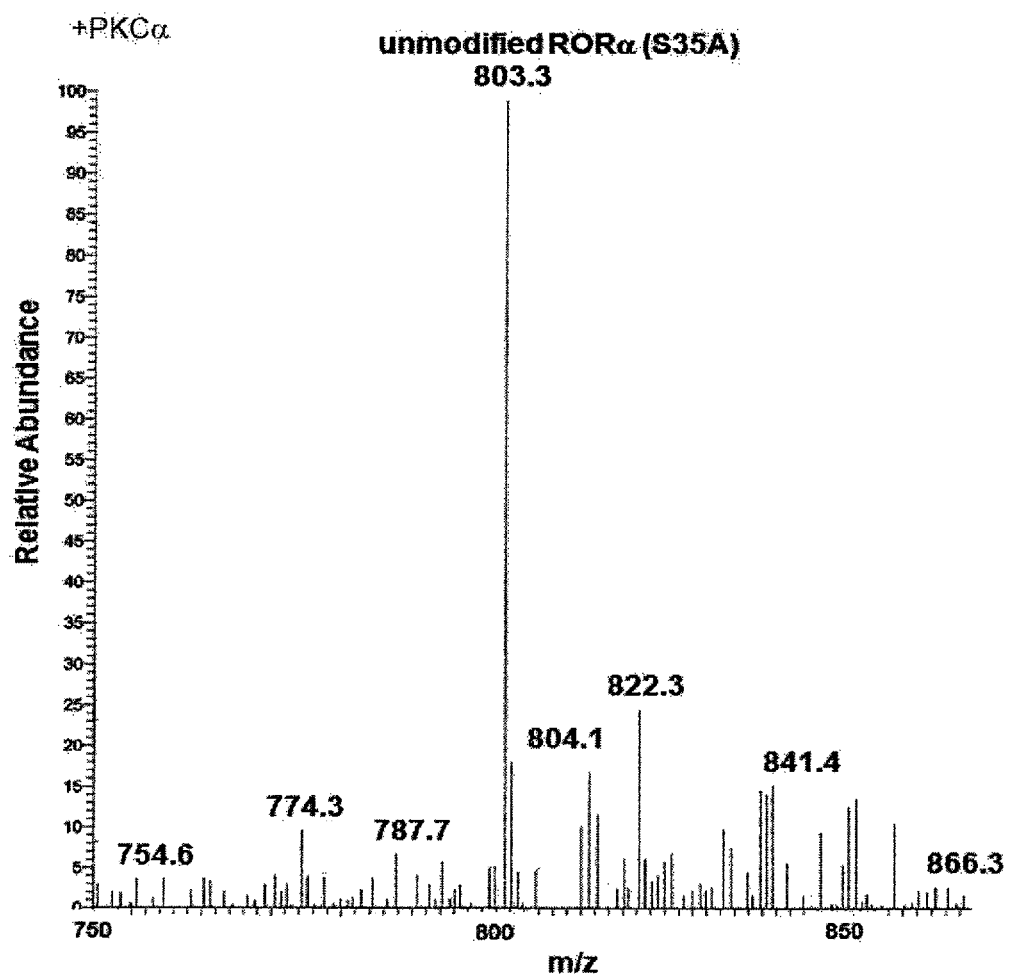

FIG. 8 shows mass spectrometifc analysis of RORαS35A peptide.

Synthesized peptides of RORαS35A (NQEAARKSE; SEQ ID NO:16) were used as substrates in the kinase assay with purified PKCα enzyme. The phosphorylated peptide samples were analyzed by mass spectrometric analysis.

Figure 9:
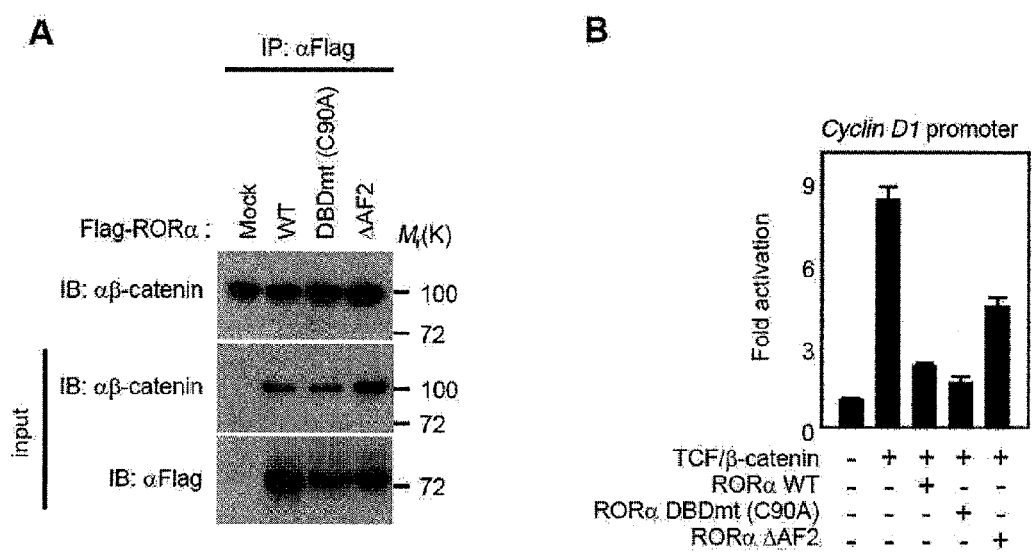

FIG. 9 shows the transcriptional activation function and DNA binding activity of RORα is not required for the repressive function on Wnt target genes (A) HCT116 cells were transfected with Flag-RORα WT, DBD mutant (C90A), or ΔAF2 mutant, and the cell extracts were immunoprecipitated with anti-Flag antibody followed by immunoblotting against anti-β-catenin antibody. (B) Introduction of RORα WT, DBD mutant (C90A), or ΔAF2 mutant inhibited the TCF/β-catenin mediated activation of the cyclin D1 promoter reporter. Data are represented as mean±s.d. for three independent experiments.

DETAILED DESCRIPTION OF THE INVENTION

To achieve the above objects, in a first aspect, the present invention provides a method for screening an anticancer agent using RORα. More specifically, the present invention provides a method for screening an anticancer agent, the method comprising the steps of culturing cells; bringing a potential substance into contact with the cells; determining whether the phosphorylation level of RORα in the cells increases as compared to that in control cells (not brought into contact with the potential substance); and selecting the potential substance as an anticancer agent if the phosphorylation level of RORα increases.

The phosphorylation level of RORα may be measured by, but not limited to, electrophoresis, fluorescence spectrometry, mass spectrometry, an immunoassay or a PCR assay. The immunoassay may be an immunoblot assay.

The phosphorylation level of RORα may be measured by analyzing the expression level of a Wnt target gene. The Wnt target gene may be any one selected from the group consisting of cyclin D1, c-myc, and c-jun. The expression level of the Wnt target gene may be analyzed by any of electrophoresis, fluorescence spectrometry, mass spectrometry, an immunoassay and a PCR assay. Preferably, the expression level of the Wnt target gene may be analyzed by an RT-PCR assay. The method for screening the anticancer agent may be applied to any cancer.

The cancer cells that are used to screen the anticancer agent are preferably cells of the same origin, but are not limited thereto. For example, cells that are used to screen an agent for treating colorectal cancer are preferably colorectal cells.

In a second aspect, the present invention provides a method of diagnosing cancer by measuring the amount of RORα in vivo. More preferably, the present invention provides a method for diagnosing cancer, the method comprising the steps of collecting cells from a subject; measuring the phosphorylation level of RORα in the cells collected from the subject; and determining that cancer is highly likely to develop if the phosphorylation level of RORα in the cells is lower than in that in cells of a normal person.

The phosphorylation level of RORα may be measured by, but not limited to, electrophoresis, fluorescence spectrometry, mass spectrometry, an immunoassay or a PCR assay. The immunoassay may be an immunoblot assay.

In a third aspect, the present invention provides a RORα-overexpressed APC$^{min/+}$ RORα mouse. The mouse is useful for studies on anticancer agents.

Hereinafter, the present invention will now be described in detail with reference to examples. However, these examples are not intended to limit the scope of the present invention as defined in the appended claims.

EXAMPLE 1

Materials and Reagents

The following antibodies were purchased from Santa Cruz Biotechnology: anti-β-catenin, cyclin D1, phospho-PKCα, and RORα. The following commercially available antibodies were used: anti-acetyl-histone H3, acetyl-histone H4, dimethyl-H3K9, and dimethyl-H3K4 antibodies (Upstate Biotechnology), anti-FLAG (Sigma), anti-RNA polymerase II (Berkeley Antibody Company), anti-Xpress (Invitrogen), and anti-phospho-Ser antibodies (Alexis). Anti-phospho-RORαS35 antibody was generated by Abmart. PKCα enzyme was purchased from Cell Signaling.

EXAMPLE 2

Mouse Strains and Generation of RORα Transgenic Mice

A pair of APC$^{min/+}$ mice were purchased from the Jackson Laboratory and housed in the animal facility of the Seoul National University according to standards of the Association for Assessment and Accreditation of Laboratory Animal Care. To construct RORα transgenic mice, full-length human RORα cDNA fused in frame with Myc tag was subcloned into the pCAGGS expression vector under the control of human CMV immediate early enhancer linked to the chicken β-actin promoter. To derive RORα transgenic mice, the pCAGGS-RORα SalI/HindIII fragment was microinjected into fertilized eggs derived from C57BL/6J mice. Integration of the transgene into the offspring genome was assessed by PCR analysis. The experiments were carried out with approval of the Institutional Animal Care and Ethics Committee.

EXAMPLE 3

Human Colon Cancer Tissue Specimens

For the analysis of phosphorylated RORα and PKCα expression in human tissue samples, 30 paired fresh frozen colon cancer tissues and matched normal mucosa tissues were selected. The frozen fresh human tissue specimens were supplied from the Liver Cancer Specimen Bank supported by National Research Resource Bank Program of the Korea Science and Engineering Foundation in the Ministry of Science and Technology. The consents to use the tissue specimens for research purposes were obtained from patients, and the utilization of the specimens for this research was authorized by the Institutional Review Board of College of Medicine, Yonsei University.

EXAMPLE 4

Purification of RORα-Containing Complex

RORα-containing complex was purified from extracts obtained from HEK293 cells stably expressing Flag-tagged RORα. As a negative control, a mock purification from HEK293 cells stably expressing an empty vector was performed. The RORα-containing complex was immunoprecipitated using anti-Flag antibody-conjugated agarose beads from extracts that were washed to remove non-specific contaminants, and the bound materials were eluted by competition with the Flag peptide (0.1 mg/ml). The bound proteins were resolved by sodium dodecyl sulphate-polyacrylamide gel electrophoresis (SDS-PAGE) and prepared for LCMS/MS analysis.

EXAMPLE 5

In Vitro Kinase Assay

In vitro kinase assays using PKCα immunoprecipitated from HEK293 cell lysates or purified PKCα enzyme as the kinase and purified GST-RORα proteins as substrates were performed at 30° C. for 30 min in kinase assay buffer containing 40 mM Tris-HCl (pH 7.5), 10 mM $MgCl_2$, 1 mM dithiothreitol (DTT), and 10 μCi of $[\gamma^{-32}P]ATP$. The reactions were terminated by adding 5× Laemmli sample buffer and by boiling for 10 min. Samples were subjected to 12% SDS-PAGE, and phosphorylated RORα was detected by autoradiography.

EXAMPLE 6

Liquid Chromatography-Mass Spectrometry

Small quantities (100 μM) of synthetic peptides (RORα or RORαS35A) were used as substrates in the kinase assay with PKCα enzyme; the reaction was stopped by 10% TCA precipitation for 10 min at 4° C. After removing the precipitates by centrifugation, the supernatants were retrieved and phosphorylated peptides in the supernatants were analyzed by LC-MS at the Korea Basic Science Institute.

EXAMPLE 7

Reporter Assays

Using a luciferase system (Promega), the luciferase activity was measured using a luminometer 48 hr after transfection and normalized by β-galactosidase expression. Values are expressed as means±standard deviations for at least three independent experiments.

EXAMPLE 8

ChIP, Two-Step ChIP, and shRNA-Coupled ChIP Assays

The ChIP, two-step ChIP, and shRNA-coupled ChIP assays were conducted as previously described (Baek et al., 2002; Kim et al., 2005).

EXAMPLE 9

Construction of Plasmids and shRNAs

RORα DBD mutant (C90A) was generated by site-directed mutagenesis, and the cysteine at Cys90 was replaced by alanine. RORαΔAF2 was generated as follows: EcoRI at the 5' ends and BamHI site at the 3' ends of RORα(amino acids 1 to 505) was amplified by PCR and the fragment was subcloned into the EcoRI/BamHI sites of 3X Flag tagged-CMV10 vector. The constructs were verified by DNA sequencing. The target sequences of shRNA against RORα, β-catenin, and non-specific (NS) shRNA are as follows: shRORα-1, 5'CGGUGCGCAGACAGAGCUAUU-3'(SEQ ID NO:1); shRORα-2, 5'-GAGGUAUCUCAGUAAC-GAAGA-3' (SEQ ID NO:2); shβ-catenin, 5'-GUCCU-GUAUGAGUGGGAAC3' (SEQ ID NO:3) (Kim et al., 2005), and shNS, 5'-CUGGACUUCCAGAAGAACAUC-3' (SEQ ID NO:4). Oligonucleotide of siPKCα duplex sequence is follows: 5'GAUCCGCGUCCUGUU-GUAUGAAAUUUCAAGAGAA-3' (SEQ ID NO:5 )(Hsieh et al., 2007).

EXAMPLE 10

Real-Time Quantitative RT-PCR

The abundance of mRNA was detected by an ABI prism 7300 system with SYBR Green (molecular probes). Primer pairs were designed to amplify 90-150 bp mRNA specific fragments, and confirmed to be unique products by melting curve analysis. The PCR conditions were 95° C. (5 min) and 40 cycles of 95° C. (30 s), 57° C. (30 s), and 72° C. (30 s).

The quantity of mRNA was calculated using the ΔΔCt method and normalized by using primers to detect β-actin or HPRT. All reactions were performed in triplicates.

EXAMPLE 11

Indirect Immunofluorescence Analysis

HCT116 cells were grown on coverslips, and were washed three times with phosphate-buffered saline (PBS) 12 hrs after transfection. The cells were then fixed with 2% paraformaldehyde in PBS for 30 min at room temperature, washed in PBS, and permeabilized with 0.5% Triton X-100 in PBS (PBS-T) for 30 min at room temperature. Blocking was performed with 3% horse serum and 10% gelatin in PBS-T for 30 min. For staining, cells were incubated with affinity-purified anti-Flag IgG for 1 hr, followed by three washes in PBS-T. The stained cells were incubated for 1 hr with fluorescein isothiocyanate-conjugated secondary antibodies (Jackson Immuno Research Lab.), followed by three washes in PBS-T.

EXAMPLE 12

Transwell Cell Migration Assay

HCT116 cells stably expressing RORα, RORαS35A, or RORαS35D were used in Transwell cell migration assays along with control cells. Transwell cell migration assay was conducted as previously described (Kim et al., 2006). Cultured cells were pretreated with Wnt5a (100 ng/ml) for 2 hr, and $2.5 \times 10^4$ HCT116 cells were loaded onto the top of a 24-well Transwell chamber assay plate (BD Biosciences). Conditioned McCoy's 5A medium containing 15% fetal bovine serum was added to the bottom chamber as a chemoattractant. After 22 hr incubation, the cells that had migrated to the lower chamber of the filter were fixed with 100% methanol, stained with DAPI, and quantified by counting the total number of cells in four different fields. All experimental studies were performed according to the manufacturer's protocols. Values are expressed as means±standard deviations for at least three independent experiments.

EXAMPLE 13

Anchorage-Independent Growth Assay

Anchorage-independent growth of HCT116 cells containing RORα, RORαS35A, or RORαS35D was determined by analyzing cellular growth in semisolid medium. $10^5$ cells were placed in McCoy's 5A media containing 0.4% noble agar containing 10% FCS. Cells were allowed to grow for 3 weeks in 5% $CO_2$, and the formation of colonies containing >50 cells was analysed.

EXAMPLE 14

Statistical Analysis

Statistical differences in test and control samples were determined by student's t-test using the Statview package (Abacus Concepts, Inc., Berkeley, Calif.).

EXAMPLE 15

Figures 1A, 1B, 1C, 1D, 1E, 1F:
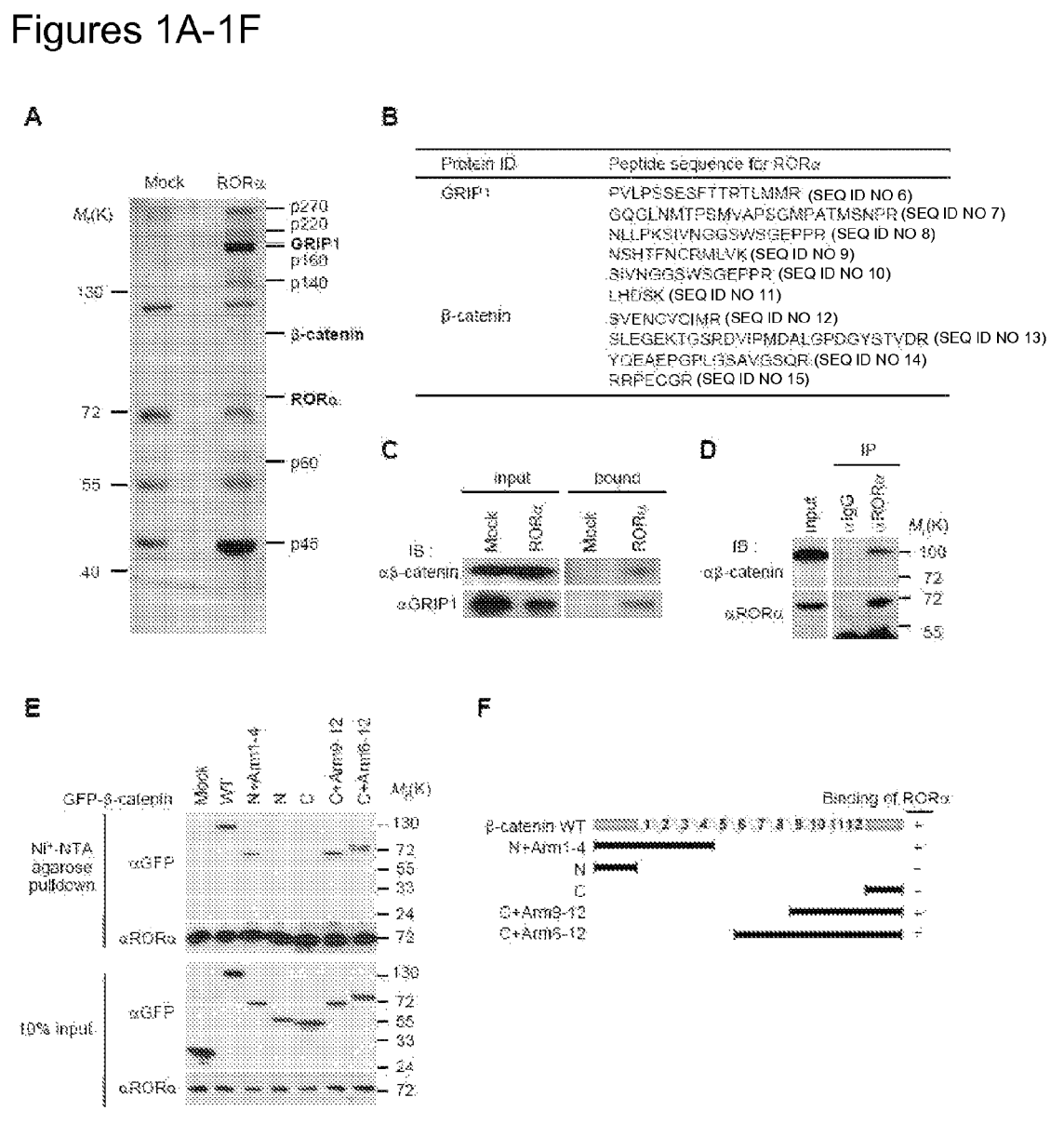

Purification of RORα-Containing Complex and Identification of β-Catenin as a Binding Partner To investigate the as-yet-unidentified functional modules of RORα, we used a Flag epitope-tag strategy to purify RORα-containing complexes. We generated cell lines that stably express Flag-tagged RORα, and incubated the extracts in anti-Flag M2 affinity gel. After washing with buffer containing increasing salt concentrations of up to 500 mM, the proteins retained on the affinity chromatography column were eluted with buffer containing Flag peptide. We employed liquid chromatography mass spectrometry/mass spectrometry (LC-MS/MS) to identify proteins in the RORα-containing complex purified from the Flag M2 affinity column. Transcriptional coactivators such as glucocorticoid receptor-interacting protein 1 (GRIP1) and β-catenin were copurified with Flag-RORα (FIGS. 1A and 1B). The presence of GRIP1 coactivator, a well-known binding partner for RORα (Atkins et al., 1999), confirms and delineates the functional link between these molecules. The binding of β-catenin to RORα was confirmed by both immunoblotting analysis of elutes and an endogenous coimmunoprecipitation assay (FIGS. 1C and 1D). The binding site mapping for RORα on β-catenin indicated that RORα interacted with the armadillo repeat domains of β-catenin, and not with the N- and C-terminal domains, which overlap with the binding sites for a subset of coactivators (FIGS. 1E and 1F). These data suggest the possibility that RORα might function as a coregulator for Wnt/β-catenin signaling. Taken together, the identification of β-catenin from RORα-containing complex suggested the probable functional link between the RORα and the Wnt/β-catenin signaling pathways.

EXAMPLE 16

Attenuation of β-Catenin Transcriptional Activity by RORα

We used the HCT116 colorectal cancer cell line in which Wnt/β-catenin signaling pathway is constitutively active to examine whether RORα is directly involved in the modulation of Wnt target genes in well-established Wnt signaling-dependent colon cancer cells. In addition to TOPFLASH reporter that has TCF/LEF binding site, cyclin D1 or c-myc gene transcripts are used as readout for Wnt signaling activation. Knockdown of β-catenin with shRNA or introduction of dominant negative form of TCF attenuated induction of cyclin D1 or c-myc gene transcripts (FIG. 2A), suggesting that increased cyclin D1 or c-myc transcript is related to Wnt signaling activation in HCT116 colon cancer cells. Introduction of RORα suppressed the induction of cyclin D1 and c-myc transcripts (FIG. 2B). The overexpression of RORα almost entirely repressed the TCF/β-catenin-mediated activation of TOPFLASH and the cyclin D1 promoter-luciferase reporters (FIGS. 2C and 2D). We silenced the expression of endogenous RORα by using shRNAs and validated the functional knockdown effects of two independent shRNAs on Wnt target genes by immunoblotting analysis (FIG. 7). In contrast to RORα overexpression, silencing of endogenous RORα by specific shRNAs caused further activation of Wnt target gene (FIG. 2E) as well as the TOPFLASH and the cyclin D1 promoter-luciferase reporters (FIGS. 2F and 2G). These data suggest that RORα is involved in the attenuation of β-catenin-mediated transcriptional activation and the overexpression of RORα has an opposing effect on the expression of Wnt target genes.

These unexpected findings led us to explore the molecular mechanism of the RORα-mediated transcriptional repression of Wnt target genes in detail. The repression of β-catenin-mediated transcriptional activation by RORα can be postulated by two mechanisms. First, RORα directly interacts with β-catenin and sequesters it away from its transcription factor, TCF in a DNA binding-independent manner. Second, RORα transrepresses β-catenin-mediated transcription by directly binding to β-catenin and possibly inhibiting the recruitment of other coactivators to the Wnt target promoters for transcriptional repression. In order to examine whether a sequestering or a transrepression process is involved in the repression of β-catenin-mediated transcriptional activation by RORα, we performed a two-step chromatin immunoprecipitation (ChIP) assay on the cyclin D1 promoter (FIG. 2H). Soluble chromatins were divided into two aliquots. One of these aliquots was immunoprecipitated with anti-RORα antibodies followed by release of the immune complexes and reimmunoprecipitated with anti-β-catenin antibodies. The other aliquot was first immunoprecipitated with anti-β-catenin antibodies followed by reimmunoprecipitation with anti-RORα antibodies. The two-step ChIP assay revealed that both RORα and β-catenin were simultaneously detected on the promoter (FIG. 2H). This supports a model in which RORα transrepresses β-catenin-mediated transcriptional activation by directly binding to β-catenin on the same promoter. To exclude the possibility that RORα completely displace TCF from β-catenin, which may lead to the inhibition of TOPFLASH reporter, coimmunoprecipitation assay was performed to examine whether the direct simultaneous interaction of β-catenin with RORα and TCF occurs. Increased expression of RORα failed to affect the interaction of β-catenin with TCF, supporting our model of simultaneous binding of β-catenin to RORα and TCF (FIG. 2I).

Additional ChIP assays on cyclin D1 promoter revealed that the overexpression of RORα significantly repressed the β-catenin-mediated transcriptional activation with a concomitant increase in RORα binding and decrease in the recruitment of RNA polymerase II (FIG. 2J). Recruitment of β-catenin and TCF was not affected by RORα overexpression. In parallel, we performed shRNA-coupled ChIP assay on cyclin D1 and c-jun promoters by employing shRNA against RORα or β-catenin (FIG. 2K). Knockdown of β-catenin resulted in the failure of histone acetylation and exhibited diminished RORα recruitment, suggesting that the recruitment of RORα to the promoter is through β-catenin. Consistent with these data, the knockdown of RORα did not change the recruitment of β-catenin; however, it induced a significant increase in the histone acetylation levels (FIG. 2K). These data suggest that the binding of RORα on the cyclin D1 and c-jun promoters is mediated through β-catenin and the binding of RORα to β-catenin confers a repressive effect on Wnt target genes.

EXAMPLE 17

RORα is Phosphorylated by Protein Kinase Cα on Serine 35

Figure 3:
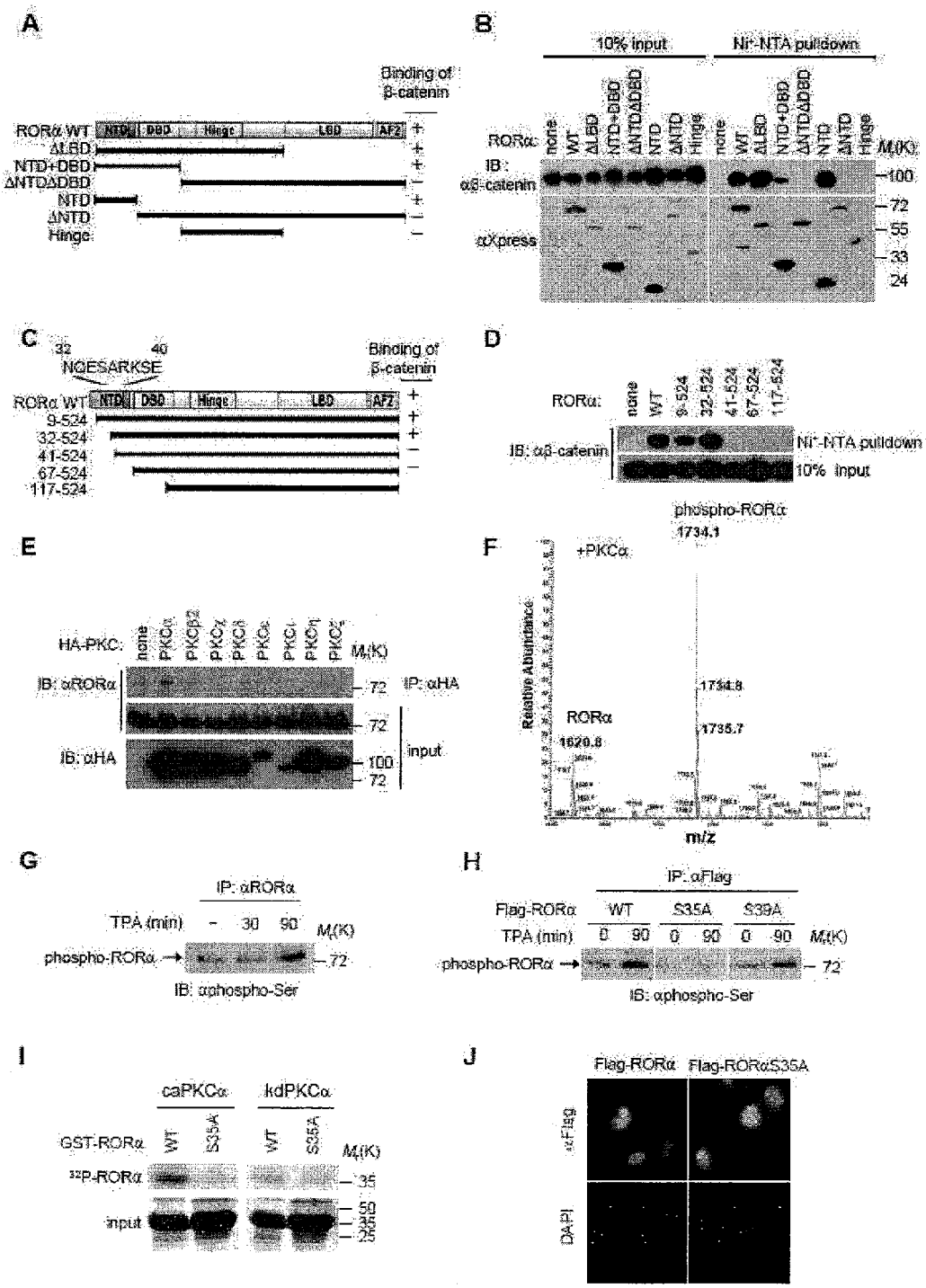
FIG. 3. RORα is phosphorylated by PKCα on serine 35

To investigate the domains of RORα that are capable of direct physical interactions with β-catenin, we prepared various RORα deletion mutants (FIG. 3A). Ni$^+$-NTA-agarose pulldown assay indicated that the N-terminal domain of RORα is responsible for β-catenin binding (FIG. 3B). We further prepared serial deletion mutants of the N-terminal domain of RORα and wished to search for molecular determinants of β-catenin binding (FIG. 3C). Fine deletion mapping revealed that N-terminal fragment of RORα spanning amino acids 32 to 41 is indispensable for β-catenin binding (FIG. 3D). Since phosphorylation is a dynamic process and the removal and addition of phosphate can change the protein binding affinity, we searched for putative phosphorylation sites. Identification of a PKC consensus site ($S/TX_{0-2}R/K_{1-3}$) in the region of RORα spanning amino acids 32 to 41 permitted us to perform a coimmunoprecipitation assay with various PKCs to investigate whether RORα binds to specific PKC isoforms. In vivo coimmunoprecipitation assays indicated that RORα specifically bound to PKCα, whereas other isoforms of PKCs, including PKCβ2, PKCχ, PKCδ, PKCε, PKCι, PKCη, and PKCξ failed to bind RORα (FIG. 3E).

The selective binding of PKCα to RORα led us to investigate whether PKCα is directly responsible for RORα phosphorylation. Mass spectrometric analysis of RORα peptide after the PKCα kinase assay revealed that RORα is phosphorylated by PKCα (FIG. 3F). The calculated molecular mass of the RORα peptide is 1620.8 Da, and addition of a phosphate group increases the mass by 113 Da. The phosphorylated RORα peptide had its main peak at 1734.1 Da. Treatment of a PKC activator, 12-O-tetradecanoylphorbol-13acetate (TPA) increased phosphorylation of endogenous RORα (FIG. 3G). RORαS35A mutant, in which serine residue is mutated to alanine, was not phosphorylated in the presence of TPA, whereas either wild-type (WT) or S39A mutant exhibited TPA-induced phosphorylation (FIG. 3H). Mass spectrometric analysis confirmed that no peaks corresponding to phosphorylated forms of the RORαS35A peptide after PKCα kinase assay were detected (FIG. 8). These data demonstrate the site-specific phosphorylation on the S35 site of RORα by PKCα.

To further examine whether PKCα directly phosphorylates RORα on S35, we performed an in vitro kinase assay using the constitutive active form of PKCα (caPKCα) or kinase deficient mutant form of PKCα (kdPKCα) immunoprecipitated from cell lysates with anti-Flag antibodies. The immunoprecipitated materials from either caPKCα or kdPKCα were incubated with bacterially expressed and purified glutathione-S-transferase (GST)RORαWT or S35A proteins. Indeed, caPKCα phosphorylated purified RORα proteins, whereas kdPKCα failed to phosphorylate RORα proteins (FIG. 3I). As expected, the RORαS35A proteins failed to be phosphorylated by caPKCα, thus confirming the S35 site-specific phosphorylation of RORα by PKCα. Immunohistochemical studies revealed that both RORα and RORαS35A exhibited an almost exclusive nuclear staining pattern in HCT116 cells, indicating that phosphorylation of RORα did not alter the nuclear localization (FIG. 3J).

EXAMPLE 18

Phosphorylation of RORα by PKCα is Crucial for Downregulation of Wnt/β-Catenin Target Genes The antibody raised against phosphorylated RORαS35 peptide specifically recognized the phosphorylated peptide as assessed by dot blot analysis (FIG. 4A). Immunoprecipitation analysis by specific, purified anti-phospho-RORαS35 IgG revealed that the wild-type, but not S35A of RORα was subject to phosphorylation by TPA treatment (FIG. 4B). Consistent with these data, introduction of caPKCα, not kdPKCα, increased phosphorylation of RORα, whereas treatment of Go6976, a specific PKCα inhibitor, abolished the TPA-induced phosphorylation of RORα, as assessed by immunoblotting against anti-phospho-RORαS35 IgG (FIGS. 4C and 4D). These data demonstrate that TPA-dependent activation of PKCα is responsible for the phosphorylation of RORα on the S35 site.

Since protein phosphorylation alters the binding affinity of proteins, we examined whether the phosphorylation of RORα affected its binding affinity toward β-catenin. RORαS35D, which mimics constitutive phosphorylation of RORα, exhibited strong binding to β-catenin, whereas RORαS35A exhibited little or no binding to β-catenin (FIG. 4E). Consistent with these data, the binding of RORα to β-catenin was significantly increased by TPA treatment and TPA-induced increased binding was almost completely abolished by treatment with Go6976 (FIG. 4F). Failure of TPA-induced phosphorylation of RORαS35A abrogated the binding of RORα to β-catenin, confirming that phosphorylation of the S35 site of RORα is crucial for the binding to β-catenin. These data clearly indicate that TPA/PKCα dependent phosphorylation of RORα modulates binding affinity of RORα toward β-catenin.

To further examine whether the RORα-mediated downregulation of Wnt target genes is affected by RORα phosphorylation that leads to increased binding to β-catenin, we performed a ChIP assay on cyclin D1 promoter with the introduction of either RORαS35A or RORαS35D. As expected, RORαS35A exhibited diminished recruitment to the promoter, whereas RORαS35D resulted in increased recruitment to the promoter (FIG. 4G). Both RORαΔAF2 mutant that has impaired transcriptional activation function and RORαC90A mutant that has impaired DNA binding activity exhibited similar binding affinity to β-catenin (FIG. 9A) and repressive functions on TCF/β-catenin-mediated activation (FIG. 9B), indicating that neither the transcriptional activity nor DNA binding activity of RORα is required for the repressive function on Wnt target genes. TPA treatment increased the recruitment of phosphorylated RORα as assessed by anti-phospho-RORαS35 IgG on the cyclin D1 promoter along with concomitant decrease in RNA polymerase II recruitment, whereas the recruitment of β-catenin on the promoter was not altered by TPA treatment (FIG. 4H).

Further, knockdown of PKCα diminished the recruitment of RORα on the cyclin D1 promoter, confirming that increased binding of RORα on the promoter is due to the PKC-dependent phosphorylation of RORα (FIG. 4I). Reverse transcriptase-polymerase chain reaction (RT-PCR) analysis indicated that TPA treatment resulted in the downregulation of the cyclin D1 transcript in HCT116 cells (FIG. 4J). In support of the phosphorylation-triggered transrepression mechanism of RORα on Wnt target genes, the knockdown of either PKCα or RORα abolished TPA-mediated downregulation of Wnt target gene expression (FIG. 4K). Taken together, these data strongly demonstrate that PKCα-dependent phosphorylation of RORα triggers increased binding of RORα to the target promoters through β-catenin and this increased binding is directly responsible for the downregulation of Wnt target genes.

EXAMPLE 19

Wnt5a Antagonizes the Canonical Wnt Signalling by Transrepression Function of RORα

Since the noncanonical Wnt signalling pathway triggered by the Wnt5a, a noncanonical Wnt ligand, activates downstream PKCs and CaMKII (Jonsson et al., 1998; Weeraratna et al., 2002), we examined whether Wnt5a induces PKCα activation leading to the following RORα phosphorylation and downregulation of Wnt target genes in colon cancer cells. Wnt5a treatment increased phosphorylation of PKCα as assessed by immunoblotting against anti-phospho-PKCα antibody that recognizes active form of PKCα (FIG. 5A). Further immunoblotting analysis against anti-phospho-RORαS35 IgG revealed that treatment of Wnt5a increased phosphorylation of RORα concomitant with downregulation of cyclin D1 expression in colon cancer cells (FIG. 5A). Consistent with these data, Wnt5a treatment reduced the expression of cyclin D1 transcript, and the knockdown of PKCα or RORα by each shRNA abolished Wnt5a-dependent downregulation of cyclin D1 transcript (FIG. 5B). These data confirm that the downregulation of Wnt target genes by Wnt5a is indeed mediated by PKCα activation. Thereafter, we examined whether Wnt5a/PKCα-dependent RORα phosphorylation is capable of suppressing β-catenin-mediated activation of Wnt target genes. Quantitative RT-PCR analysis revealed that RORαS35D, not RORαS35A, induced the downregulation of the cyclin D1 transcript (FIG. 5C). These data suggest that RORα mediates Wnt5a-dependent suppressive effects on the canonical Wnt signaling pathway in a phosphorylation-dependent manner in colon cancer cells.

Given that RORα exerts its repressive effect by directly binding to β-catenin on the promoter and the binding site for RORα on β-catenin resides in the armadillo repeat domains of β-catenin that demonstrate overlap with the binding sites of a subset of coactivators (FIG. 1E), the transrepression mechanism of RORα on β-catenin might be achieved by competition for β-catenin binding with a subset of coactivators. ChIP assay on the cyclin D1 promoter revealed that treatment with Wnt5a or TPA increased the recruitment of phosphorylated RORα to the promoter, whereas the recruitment of CBP, p300, and pCAF coactivators to the promoter was significantly decreased (FIG. 5D). Indeed, the TPA or Wnt5a-dependent phosphorylation of RORα attenuated the β-catenin-dependent transcriptional activation, leading to the increased methylation of histone H3K9 and decreased RNA polymerase II recruitment (FIG. 5D). These results indicate that the downregulation of Wnt target genes is a direct consequence of RORα binding triggered by phosphorylation, and the transrepression mechanism of RORα on β-catenin is achieved, at least in part, by competition with a subset of coactivators for β-catenin binding and possibly recruitment of histone lysine methyltransferases for transcriptional repression.

As upregulation of cyclin D1, c-myc, or c-jun is correlated with cell proliferation and migration, we next examined whether phosphorylation of RORα could inhibit cellular migration. Transwell cell migration assay that measured the increase in cell number for RORα, RORαS35A, or RORαS35D-expressing HCT116 colon cancer cells revealed that Wnt5a treatment attenuated migration of HCT116 colon cancer cells compared to non-treated cells and RORαS35D-expressing cells exhibited a significant decrease of cell migration in the presence of Wnt5a (FIG. 5E and data not shown). These results suggest that a mechanism underlying RORα-mediated inhibition of cell migration is, at least in part, through the inhibition of Wnt target genes in a phosphorylation-dependent manner.

We then considered other properties known to be important for cell and tumor growth. As anchorage-independent growth is an important property of tumor cell growth, we asked whether RORαS35D, but not RORαS35A could suppress the colony-forming ability of HCT116 cells in soft agar. Consistent with the anti-proliferative properties of RORαS35D, HCT116 cells expressing RORαS35D grew significantly slower than control cells (FIG. 5F and data not shown). Furthermore, the size of the colonies formed by RORαS35 D expressing cells was much smaller than those formed by the control cells. These data suggest that RORα has a significant role in regulating cellular growth in phosphorylation-dependent manner.

EXAMPLE 20

Reduction of RORα Phosphorylation is Frequent in Human Colorectal Cancers

To find the clinical relevance of our findings, we examined the expression of phosphorylated RORα and PKCα in the 30 colorectal cancer tissues and matched normal mucosa specimens. Immunoblot analysis against anti-phospho-RORαS35

IgG revealed the reduction of RORα phosphorylation in 22 out of 30 (>73%) cases, and of these 22 cases, 14 cases of them (>46%) exhibited the reduction of phosphorylation of PKCα (Table 1 and FIG. 6A). We further investigated the expression of Wnt target genes in these normal and tumor samples by quantitative RT-PCR. All of the cases in which reduction of RORα phosphorylation and PKCα inactivation exhibited the increased expression of Wnt target genes (Table 1). Wnt5a expression has been reported to be down-regulated in multiple tumors including colon, breast, and prostate, whereas it is upregulated in brain, stomach, kidney, and skin tumors (Blanc et al., 2005; Iozzo et al., 1995; Kremenevskaja et al., 2005). Further quantitative RT-PCR analysis supported the idea that downregulation of Wnt5a in colon tumor correlates with inactivation of PKCα and reduction of RORα phosphorylation (Table 1). These data suggest that reduction of RORα phosphorylation along with inactivation of PKCα and downregulation of Wnt5a is frequent event in colorectal cancer.

TABLE 1

| | | | Fold (Tumor/Normal tissues) | | | |
|---|---|---|---|---|---|---|
| | phospho- | phospho- | | Wnt targets | | |
| No. | RORα | PKCα | Wnt5a | CyclinD1 | c-Myc | c-Jun |
| 1 | Δ | Δ | +42Δ | −1.4▼ | +56Δ | +18Δ |
| 2 | NC | Δ | +66Δ | +42Δ | +12Δ | +56Δ |
| 3 | NC | Δ | +160Δ | +6.0Δ | +49Δ | +58Δ |
| 4 | ▼ | Δ | +16Δ | −69▼ | +11Δ | +2.3Δ |
| 5 | ▼ | ▼ | −42▼ | +120Δ | +25Δ | NC |
| 6 | ▼ | ▼ | −66▼ | +13Δ | +16Δ | +4.4Δ |
| 7 | ▼ | ▼ | −6.3▼ | +8.4Δ | +132Δ | +20Δ |
| 8 | NC | Δ | +32Δ | +45Δ | +50Δ | NC |
| 9 | ▼ | ▼ | −18▼ | +9.1Δ | +430Δ | NC |
| 10 | ▼ | ▼ | −20▼ | +1.4Δ | +1.8Δ | +20Δ |
| 11 | ▼ | ▼ | −24▼ | +6.7Δ | +1.3Δ | +4.9Δ |
| 12 | NC | NC | +13Δ | −2.5▼ | −1.8▼ | −1.7▼ |
| 13 | ▼ | ▼ | −11▼ | +1.3Δ | +8.4Δ | +5.4Δ |
| 14 | ▼ | ▼ | −13▼ | NC | +7.4Δ | +3.3Δ |
| 15 | NC | Δ | +16Δ | +4.6Δ | +6.1Δ | +11Δ |
| 16 | ▼ | NC | +190Δ | −1.8▼ | +9.4Δ | +10Δ |
| 17 | ▼ | NC | +49Δ | +3.2Δ | +14Δ | NC |
| 18 | ▼ | ▼ | NC | +3.6Δ | +5.4Δ | +1.7Δ |
| 10 | ▼ | ▼ | −23▼ | +3.0Δ | +9.4Δ | +1.8Δ |
| 20 | NC | ▼ | +47Δ | NC | NC | NC |
| 21 | Δ | ▼ | +38Δ | +3.4Δ | +2.9Δ | +32Δ |
| 22 | ▼ | NC | +62Δ | −1.3▼ | +8.7Δ | +6.8Δ |
| 23 | ▼ | ▼ | −4.5▼ | +1.7Δ | +1.2Δ | NC |
| 24 | ▼ | NC | −4.0▼ | NC | +5.1Δ | +2.5Δ |
| 25 | ▼ | ▼ | −1.2▼ | +20Δ | +6.3Δ | +33Δ |
| 26 | ▼ | Δ | NC | −18▼ | −1.8▼ | NC |
| 27 | ▼ | NC | −99▼ | −1.7▼ | +3.7Δ | +34Δ |
| 28 | ▼ | ▼ | −3.5▼ | +1.9Δ | +1.5Δ | +13Δ |
| 29 | ▼ | NC | NC | +8.5Δ | NC | +8.1Δ |
| 30 | ▼ | ▼ | −3.7▼ | +2.1Δ | +2.0Δ | +6.5Δ |

EXAMPLE 21

The Reduced Polyp Development in APC$^{min/+}$ RORα Transgenic Mouse Compared with Those in APC$^{min/+}$ Mouse To examine whether tumor suppressive function of RORα is applied to spontaneous intestinal tumorigenesis of mouse model, we generated APC$^{min/+}$ mice crossed with RORα transgenic mice and analyzed sex- and age-matched mice. We generated transgenic mice expressing a human RORα cDNA, and confirmed the increase of RORα expression in colon and intestine tissues (data not shown). APC$^{min/+}$ mice die within 24 weeks of age, whereas mortality of APC$^{min/+}$ RORα transgenic mice was decreased compared with APC$^{min/+}$ littermate controls (FIG. 6B). We quantified the number of polyps by stereoscopic microscopy, and found the decrease of the number of visible polyps (>1.0 mm in diameter) in the intestines or colon of APC$^{min/+}$ RORα transgenic mice compared with that in APC$^{min/+}$ mice (FIG. 6C). These data support the notion that RORα influences the Wnt signalling mediated tumor formation and growth by suppressive function of Wnt signaling. Taken together, RORα affects modulation of cell and tumor growth in APC$^{min/+}$ mouse model of intestinal tumorigenesis.

References

Atkins, G. B., Hu, X., Guenther, M. G., Rachez, C., Freedman, L. P., and Lazar, M. A. (1999). Coactivators for the orphan nuclear receptor RORα. Mol. Endocrinol. 13, 1550-1557.

Baek, S. H., Ohgi, K. A., Rose, D. W., Koo, E. H., Glass, C. K., and Rosenfeld, M. G. (2002). Exchange of N-CoR corepressor and Tip60 coactivator complexes links gene expression by NF-κB and beta-amyloid precursor protein. Cell 110, 55-67.

Behrens, J., von Kries, J. P., Kuhl, M., Bruhn, L., Wedlich, D., Grosschedl, R, and Birchmeier, W. (1996). Functional interaction of beta-catenin with the transcription factor LEF-1. Nature 382, 638-642.

Blanc, E., Roux, G. L., Bénard, J., and Raguénez, G. (2005). Low expression of Wnt-5a gene is associated with high-risk neuroblastoma. Oncogene 24, 1277-1283.

Blumberg, B., and Evans, R. M. (1998). Orphan nuclear receptors-new ligands and new possibilities. Genes Dev. 12, 3149-3155.

Dejmek, J., Dejmek, A., Säfholm, A., Sjölander, A., and Andersson, T. (2005). Wnt-5a protein expression in primary dukes B colon cancers identifies a subgroup of patients with good prognosis. Cancer Res. 65, 9142-9146.

Doulazmi, M., Capone, F., Frederic, F., Boukhtouche, J., Lemaigre-Dubreuil, Y., and Mariani, J. (2006). Cerebellar purkinje cell loss in heterozygous rora+/−mice: a longitudinal study. J. Neurogenet. 20, 1-17.

Firestein, R., Bass, A. J., Kim, S. Y., Dunn, I. F., Silver, S. J., Guney, I., Freed, E., Ligon, A. H., Vena, N., Ogino, S., et al. (2008). CDK8 is a colorectal cancer oncogene that regulates beta-catenin activity. Nature 455, 547-551.

Fodde, R., Edelmann, W., Yang, K., van Leeuwen, C., Carlson, C., Renault, B., Breukel, C., Alt, E., Lipkin, M., Khan, P. M., et al. (1994). A targeted chain-termination mutation in the mouse Apc gene results in multiple intestinal tumors. Proc. Natl. Acad. Sci. USA 91, 89698973.

Giguère, V. (1999). Orphan nuclear receptors: from gene to function. Endocrine Reviews 20, 689-725.

Giguère, V., Tini, M., Flock, G., Ong, E., Evans, R. M., and Otulakowski, G. (1994). Isoformspecific amino-terminal domains dictate DNA-binding properties of ROR alpha, a novel family of orphan hormone nuclear receptors. Genes Dev. 8, 538-553.

Giles, R. H., van Es, J. H., and Clevers, H. (2003). Caught up in a Wnt storm: Wnt signaling in cancer. Biochim. Biophys Acta. 1653, 1-24.

Gold, D. A., Baek, S. H., Schork, N. J., Rose, D. W., Larsen, D. D., Sachs, B. D., Rosenfeld, M. G., and Hamilton, B. A. (2003). RORα coordinates reciprocal signaling in cerebellar development through sonic hedgehog and calcium-dependent pathways. Neuron 40, 1119-1131.

Groden, J., Thliveris, A., Samowitz, W., Carlson, M., Gelbert, L., Albertsen, H., Joslyn, G., Stevens, J., Spirio, L., Robertson, M., et al. (1991). Identification and characterization of the familial adenomatous polyposis coli gene. Cell 66, 589-600.

Hamilton, B. A., Frankel, W. N., Kerrebrock, A. W., Hawkins, T. L., FitzHugh, W., Kusumi, K., Russell, L. B., Mueller, K. L., van Berkel, V., Birren, B. W., et al. (1996). Disruption of the nuclear hormone receptor ROR alpha in staggerer mice. Nature 379, 736-739.

Hsieh, Y. H., Wu, T. T., Huang, C. Y., Hsieh, Y. S., Hwang, J. M., and Liu, J. Y. (2007). p38 mitogen-activated protein kinase pathway is involved in protein kinase C alpha-regulated invasion in human hepatocellular carcinoma cells. Cancer Res. 67, 4320-4327.

Iozzo, R. V., Eichstetter, I., and Danielson, K. G. (1995). Aberrant expression of the growth factor Wnt-5A in human malignancy. Cancer Res. 55, 3495-3499.

Ito, K., Lim, A. C., Salto-Tellez, M., Motoda, L., Osato, M., Chuang, L. S., Lee, C. W., Voon, D. C., Koo, J. K., Wang, H., et al. (2008). RUNX3 attenuates beta-catenin/T cell factors inintestinal tumorigenesis. Cancer Cell 14, 226-237.

Jonsson, M., Smith, K., and Harris, A. L. (1998). Regulation of Wnt5a expression in human mammary cells by protein kinase C activity and the cytoskeleton. British Journal of Cancer. 78, 430-438.

Kühl, M., Sheldahl, L. C., Park, M., Miller, J. R., and Moon, R. T. (2000). The Wnt/$Ca^{2+}$ pathway: a new vertebrate Wnt signaling pathway takes shape. Trends Genet. 16, 279-283.

Kim, J. H., Choi, H. J., Kim, B., Kim, M. H., Lee, J. M., Kim, I. S., Lee, M. H., Choi, S. J., Kim, K. I., Kim, S. I., et al. (2006). Roles of SUMOylation of a reptin chromatin remodeling complex in cancer metastasis. Nat. Cell. Biol. 8, 631-639.

Kim, J. H., Kim, B., Ling, C., Choi, H. J., Ohgi, K. A., Chen, C., Chung, C. H., Huber, O., Rose, D. W., Sawyers, C. L., et al. (2005). Transcriptional regulation of a metastasis suppressor gene by Tip60 and beta-Catenin Complexes. Nature 434, 921-926.

Kinzler, K. W., Nilbert, M. C., Su, L. K., Vogelstein, B., Bryan, T. M., Levy, D. B., Smith, K. J., Preisinger, A. C., Hedge, P., McKechnie, D., et al. (1991). Identification of FAP locus gene from chromosome 5q21. Science 253, 661-665.

Klaus, A., and Birchmeier, W. (2008). Wnt signalling and its impact on development and cancer. Nat. Rev. Cancer. 8, 387-398.

Korinek, V., Barker, N., Morin, J. P., van Wichen, D., de Weger, R, Kinzler, K. W., Vogelstein, B., and Clevers, H. (1997). Constitutive transcriptional activation by a β-catenin-Tcf complex in APC/colon carcinoma. Science 275, 1784-1787.

Kremenevskaja, N., von Wasielewski, R., Rao, A. S., Schöfl, C., Andersson, T., and Brabant, G. (2005). Wnt-5a has tumor suppressor activity in thyroid carcinoma. Oncogene 24, 21442154.

Lau, P., Nixon, S. J., Parton, R. J., and Muscat, G. E. (1994). RORα regulates the expression of genes involved in lipid homeostasis in skeletal muscle cells: caveolin-3 and CPT-1 are direct targets of ROR. J. Biol. Chem. 279, 36828-36840.

Leitges, M. (2007). Functional PKC in vivo analysis using deficient mouse models. Biochem. Soc. Trans. 35, 1018-1020.

Liang, H., Coles, A. H., Zhu, Z., Zayas, J., Jurecic, R., Kang, J., and Jones, S. N. (2007). Noncanonical Wnt signaling promotes apoptosis in thymocyte development. J. Exp. Med. 204, 3077-3084.

Liu, G., Bafico, A., and Aaronson, S. A. (2005). The mechanism of endogenous receptor activation functionally distinguishes prototype canonical and noncanonical Wnts. Mol. Cell Biol. 25, 3475-3482.

Major, M. B., Camp, N. D., Berndt, J. D., Yi, X., Goldenberg, S. J., Hubbert, C., Biechele, T. L., Gingras, A. C., Zheng, N., Maccoss, M. J., et al. (2007). Wilms tumor suppressor WTX negatively regulates WNT/beta-catenin signaling. Science 316, 1043-1046.

Mangelsdorf, D. J., Thummel, C., Beato, M., Herrlich, P., Schutz, G., Umesono, K., Blumberg, B., Kastner, P., Mark, M., Chambon, P., et al. (1995). The nuclear receptor superfamily: the second decade. Cell 83, 835-839.

Matysiak-Scholze, U., and Nehls, M. (1997). The structural integrity of RORα isoforms is mutated in staggerer mice: cerebellar coexpression of RORα1 and RORα4. Genomics 43, 78-84.

Mikels, A. J., and Nusse, R. (2006). Purified Wnt5a protein activates or inhibits beta-catenin-TCF signaling depending on receptor context. PLoS Biol. 4, 570-582.

Molenaar, M., van de Wetering, M., Oosterwegel, M., Peterson-Maduro, J., Godsave, S., Korinek, V., Roose, J., Destree, O., and Clevers, H. (1996). XTcf-3 transcription factor mediates beta-catenin-induced axis formation in *Xenopus* embryos. Cell 86, 391-399.

Moon, R. T., Bowerman, B., Boutros, M., and Perrimon, N. (2002). The promise and perils of Wnt signaling through beta-catenin. Science 296, 1644-1646.

Morin, P. J., Sparks, A. B., Korinek, V., Barker, N., Clevers, H., Vogelstein, B., and Kinzler, K. W. (1997). Activation of beta-catenin-Tcf signaling in colon cancer by mutations in beta-catenin or APC. Science 275, 1787-1790.

Nemeth, M. J., Topol, L., Anderson, S. M., Yang, Y., and Bodine, D. M. (2007). Wnt5a inhibits canonical Wnt signaling in hematopoietic stem cells and enhances repopulation. Proc. Natl. Acad. Sci. USA 104, 15436-15441.

Orford, K., Crockett, C., Jensen, J. P., Weissman, A. M., and Byers, S. W. (1997). Serine phosphorylation-regulated ubiquitination and degradation of beta-catenin. J. Biol. Chem. 272, 24735-24738.

Oster, H., and Leitges, M. (2006). Protein kinase C alpha but not PKCzeta suppresses intestinal tumor formation in ApcMin/+ mice. Cancer Res. 66, 6955-6963.

Peifer, M., and Polakis, P. (2000). Signaling in oncogenesis and embryogenesis-a look outside the nucleus. Science 287.

Polakis, P. (2000). Wnt signaling and cancer. Genes Dev. 14, 1837-1851.

Salic, A., Lee, E., Mayer, L., and Kirschner, M. W. (2000). Control of β-catenin stability: reconstitution of the cytoplasmic steps of the wnt pathway in *Xenopus* egg extracts. Mol. Cell 5, 523-532.

Shibata, H., Toyama, K., Shioya, H., Ito, M., Hirota, M., Hasegawa, S., Matsumoto, H., Takano, H., Akiyama, T., Toyoshima, K., et al. (1997). Rapid colorectal adenoma formation initiated by conditional targeting of the Apc gene. Science 278, 120-123.

Slusarski, D. C., Corces, V. G., and Moon, R. T. (1997). Interaction of Wnt and a Frizzled homologue triggers G-protein-linked phosphatidylinositol signalling. Nature 390, 410-413.

Steinmayr, M., André, E., Conquet, F., Rondi-Reig, L., Delhaye-Bouchaud, N., Auclair, N., Daniel, H., Crepel, F., Mariani, J., Sotelo, C., et al. (1998). Staggerer phenotype in retinoid-related orphan receptor α-deficient mice. Proc. Natl. Acad. Sci. USA 95, 3960-3965.

Su, L. K., Kinzler, K. W., Vogelstein, B., Preisinger, A. C., Moser, A. R., Luongo, C., Gould, K. A., and Dove, W. F.

(1992). Multiple intestinal neoplasia caused by a mutation in the murine homolog of the APC gene. Science 256, 668-670.

Torres, M. A., Yang-Snyder, J. A., Purcell, S. M., DeMarais, A. A., and McGrew, L. L. (1996). Activities of the Wnt-1 class of secreted signaling factors are antagonized by the Wnt-5A class and by a dominant negative cadherin in early *Xenopus* development. J. Cell Biol. 133, 1123-1137.

van de Wetering, M., Sancho, E., Verweij, C., de Lau, W., Oving, I., Hurlstone, A., van der Horn, K., Batlle, E., Coudreuse, D., Haramis, A. P., et al. (2002). The β-catenin/TCF-4 complex imposes a crypt progenitor phenotype on colorectal cancer cells. Cell 111, 241-250.

Weeraratna, A. T., Jiang, Y., Hostetter, G., Rosenblatt, K., Duray, P., Bittner, M., and Trent, J. M. (2002). Wnt5a signaling directly affects cell motility and invasion of metastatic melanoma. Cancer Cell. 1, 279-288.

Westfall, T. A., Brimeyer, R., Twedt, J., Gladon, J., Olberding, A., Furutani-Seiki, M., and Slusarski, D. C. (2003). Wnt-5/pipetail functions in vertebrate axis formation as a negative regulator of Wnt/beta-catenin activity. J. Cell Biol. 162, 889-898.

Willert, K., Brown, J. D., Danenberg, E., Duncan, A. W., Weissman, I. L., Reya, T., Yates, J. R., and Nusse, R. (2003). Wnt proteins are lipid-modified and can act as stem cell growth factors. Nature 423, 448-452.

What is claimed is:

1. A method for screening an anticancer agent, the method comprising the steps of:
    culturing cells;
    bringing a potential substance into contact with the cells;
    determining whether the phosphorylation level of RORα in the cells increases as compared to that in control cells (not brought into contact with the potential substance) by measuring phospho-RORα S35 (RORα phosphorylated at serine 35) in an immunoassay using an antibody raised against a phospho-RORα S35 peptide consisting of SEQ ID NO:18; and
    selecting the potential substance as an anticancer agent if the phosphorylation level of RORα in the cells increases.

2. The method of claim 1, wherein the immunoassay is an immunoblot assay.

3. The method of claim 1, wherein the cells are colorectal cancer cells.

* * * * *

SEQUENCE LISTING

```
<160> NUMBER OF SEQ ID NOS: 18

<210> SEQ ID NO 1
<211> LENGTH: 21
<212> TYPE: RNA
<213> ORGANISM: Artificial Sequence
<220> FEATURE:
<223> OTHER INFORMATION: shROR alpha 1

<400> SEQUENCE: 1
cggugcgcag acagagcuau u                                              21

<210> SEQ ID NO 2
<211> LENGTH: 21
<212> TYPE: RNA
<213> ORGANISM: Artificial Sequence
<220> FEATURE:
<223> OTHER INFORMATION: shROR alpha 2

<400> SEQUENCE: 2
gagguaucuc aguaacgaag a                                              21

<210> SEQ ID NO 3
<211> LENGTH: 19
<212> TYPE: RNA
<213> ORGANISM: Artificial Sequence
<220> FEATURE:
<223> OTHER INFORMATION: sh beta catenin

<400> SEQUENCE: 3
guccuguaug agugggaac                                                 19

<210> SEQ ID NO 4
<211> LENGTH: 21
<212> TYPE: RNA
<213> ORGANISM: Artificial Sequence
<220> FEATURE:
<223> OTHER INFORMATION: shNS

<400> SEQUENCE: 4
cuggacuucc agaagaacau c                                              21

<210> SEQ ID NO 5
<211> LENGTH: 34
<212> TYPE: RNA
<213> ORGANISM: Artificial Sequence
<220> FEATURE:
<223> OTHER INFORMATION: siPKC alpha

<400> SEQUENCE: 5
gauccgcguc cuguuguaug aaauuucaag agaa                                34
```

<210> SEQ ID NO 6
<211> LENGTH: 17
<212> TYPE: PRT
<213> ORGANISM: Homo sapiens

<400> SEQUENCE: 6

Pro Val Leu Pro Ser Ser Glu Ser Phe Thr Thr Arg Thr Leu Met Met
1               5                   10                  15

Arg

<210> SEQ ID NO 7
<211> LENGTH: 24
<212> TYPE: PRT
<213> ORGANISM: Homo sapiens

<400> SEQUENCE: 7

Gly Gln Gly Leu Asn Met Thr Pro Ser Met Val Ala Pro Ser Gly Met
1               5                   10                  15

Pro Ala Thr Met Ser Asn Pro Arg
            20

<210> SEQ ID NO 8
<211> LENGTH: 19
<212> TYPE: PRT
<213> ORGANISM: Homo sapiens

<400> SEQUENCE: 8

Asn Leu Leu Pro Lys Ser Ile Val Asn Gly Gly Ser Trp Ser Gly Glu
1               5                   10                  15

Pro Pro Arg

<210> SEQ ID NO 9
<211> LENGTH: 12
<212> TYPE: PRT
<213> ORGANISM: Homo sapiens

<400> SEQUENCE: 9

Asn Ser His Thr Phe Asn Cys Arg Met Leu Val Lys
1               5                   10

<210> SEQ ID NO 10
<211> LENGTH: 14
<212> TYPE: PRT
<213> ORGANISM: Homo sapiens

<400> SEQUENCE: 10

Ser Ile Val Asn Gly Gly Ser Trp Ser Gly Glu Pro Pro Arg
1               5                   10

<210> SEQ ID NO 11
<211> LENGTH: 5
<212> TYPE: PRT
<213> ORGANISM: Homo sapiens

<400> SEQUENCE: 11

Leu His Asp Ser Lys
1               5

<210> SEQ ID NO 12
<211> LENGTH: 10
<212> TYPE: PRT
<213> ORGANISM: Home sapiens

```
<400> SEQUENCE: 12

Ser Val Glu Asn Cys Val Cys Ile Met Arg
1               5                   10

<210> SEQ ID NO 13
<211> LENGTH: 28
<212> TYPE: PRT
<213> ORGANISM: Homo sapiens

<400> SEQUENCE: 13

Ser Leu Glu Gly Glu Lys Thr Gly Ser Arg Asp Val Ile Pro Met Asp
1               5                   10                  15

Ala Leu Gly Pro Asp Gly Tyr Ser Thr Val Asp Arg
            20                  25

<210> SEQ ID NO 14
<211> LENGTH: 17
<212> TYPE: PRT
<213> ORGANISM: Homo sapiens

<400> SEQUENCE: 14

Tyr Gln Glu Ala Glu Pro Gly Pro Leu Gly Ser Ala Val Gly Ser Gln
1               5                   10                  15

Arg

<210> SEQ ID NO 15
<211> LENGTH: 7
<212> TYPE: PRT
<213> ORGANISM: Homo sapiens

<400> SEQUENCE: 15

Arg Arg Pro Glu Cys Gly Arg
1               5

<210> SEQ ID NO 16
<211> LENGTH: 9
<212> TYPE: PRT
<213> ORGANISM: Artificial Sequence
<220> FEATURE:
<223> OTHER INFORMATION: synthesized peptides of RORalpha

<400> SEQUENCE: 16

Asn Gln Glu Ala Ala Arg Lys Ser Glu
1               5

<210> SEQ ID NO 17
<211> LENGTH: 9
<212> TYPE: PRT
<213> ORGANISM: Artificial Sequence
<220> FEATURE:
<223> OTHER INFORMATION: Synthesized Peptide

<400> SEQUENCE: 17

Asn Gln Glu Ser Ala Arg Lys Ser Glu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthesized Peptide
```

-continued

```
<400> SEQUENCE: 18

Pro Leu Asn Gln Glu Ser Ala Arg
1               5
```